(12) United States Patent
Baumfalk et al.

(10) Patent No.: US 8,252,582 B2
(45) Date of Patent: Aug. 28, 2012

(54) DISPOSABLE BIOREACTOR COMPRISING A SENSOR ARRANGEMENT

(75) Inventors: Reinhard Baumfalk, Goettingen (DE);
Oscar-Werner Reif, Hannover (DE);
Thomas Scheper, Hannover (DE);
Daniel Riechers, Hannover (DE);
Russell Hayden, Stratford, CT (US);
Philip Nuzzo, Southington, CT (US)

(73) Assignee: Sartorius Stedim Biotech GmbH (DE)

( * ) Notice: Subject to any disclaimer, the term of this patent is extended or adjusted under 35 U.S.C. 154(b) by 0 days.

(21) Appl. No.: 12/226,463

(22) PCT Filed: Apr. 24, 2007

(86) PCT No.: PCT/EP2007/003563
§ 371 (c)(1),
(2), (4) Date: Oct. 17, 2008

(87) PCT Pub. No.: WO2007/131593
PCT Pub. Date: Nov. 22, 2007

(65) Prior Publication Data
US 2009/0075362 A1    Mar. 19, 2009

(30) Foreign Application Priority Data

May 11, 2006  (DE) .................... 10 2006 022 307

(51) Int. Cl.
*C12M 3/00* (2006.01)
*G01N 15/06* (2006.01)
*G01N 27/00* (2006.01)
*G01N 7/10* (2006.01)

(52) U.S. Cl. ................. 435/289.1; 422/68.1; 422/82.01; 422/82.05; 422/83

(58) Field of Classification Search ................. 422/68.1, 422/82.01, 82.05, 83; 435/289.1
See application file for complete search history.

(56) References Cited

U.S. PATENT DOCUMENTS

| 4,187,846 A | * | 2/1980 | Lolachi et al. | 604/411 |
| 6,379,340 B1 | * | 4/2002 | Zinger et al. | 604/246 |

(Continued)

FOREIGN PATENT DOCUMENTS

DE    202005013904 U1    2/2006

(Continued)

OTHER PUBLICATIONS

Ulber et al., Anal. Bioanal. Chem. 376, 2003, pp. 342-348.*

(Continued)

*Primary Examiner* — Nathan Bowers
*Assistant Examiner* — Gautam Prakash
(74) *Attorney, Agent, or Firm* — Gerald E. Hespos; Michael J. Porco

(57) ABSTRACT

The invention relates to a disposable bioreactor comprising a reversible, externally attachable sensor arrangement for measuring a physical variable of a contained medium. A sensor adapter (28) for receiving an electronic sensor arrangement (34, 38; 42; 44a, 44b, 46, 48) interacting with the medium cross-flowing the peripheral lines (14, 16, 18), by means of an inner delimiting surface (32a, 32b; 42; 44a, 44b, 46, 48) of the sensor adapter, is integrated into at least one of the peripheral lines (14, 16, 18) of the bioreactor which is used to supply or discharge the medium. Said sensor adapter (28) is mounted on the peripheral line (14, 16, 18) as an insert extending the peripheral line (14, 16, 18) and which can be cross-flown by the contained medium.

12 Claims, 2 Drawing Sheets

U.S. PATENT DOCUMENTS

Figure 1:
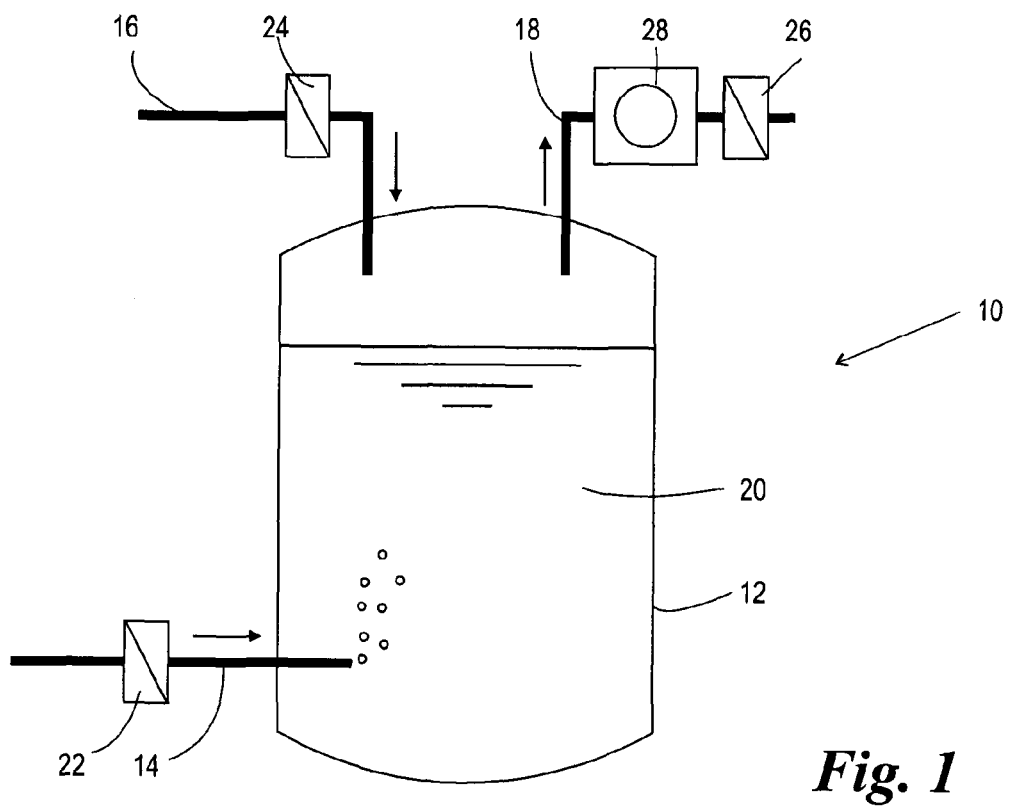

| | | | |
|---|---|---|---|
| 6,391,638 B1* | 5/2002 | Shaaltiel | 435/383 |
| 7,293,477 B2* | 11/2007 | Furey et al. | 73/863.86 |
| 7,303,544 B2* | 12/2007 | Butikofer et al. | 604/93.01 |
| 7,674,254 B2* | 3/2010 | Baumfalk et al. | 604/533 |
| 2003/0023149 A1 | 1/2003 | Montemagno | |
| 2005/0163667 A1 | 7/2005 | Krause | |
| 2005/0239198 A1* | 10/2005 | Kunas et al. | 435/297.1 |
| 2006/0240546 A1* | 10/2006 | Goodwin et al. | 435/289.1 |

FOREIGN PATENT DOCUMENTS

| | | |
|---|---|---|
| WO | 2005015130 A2 | 2/2002 |
| WO | WO 2005/108549 A1 | 11/2005 |
| WO | WO 2005/118771 A2 | 12/2005 |
| WO | WO 2005/123258 A1 | 12/2005 |
| WO | WO 2005/118771 A3 | 2/2006 |
| WO | WO 2006/017951 A1 | 2/2006 |
| WO | WO 2006/075030 * | 7/2006 |

OTHER PUBLICATIONS

Instrument Engineers' Handbook, Fourth Edition, vol. One: Process Measurement and Analysis, Béla G. Lipták (Ed.), CRC Press, 2003.*

"Two-dimensional fluorescence spectroscopy: A novel approach for controlling fed-batch cultivations"; *Elsevier, Journal of Biotechnology*; Jul. 15, 2005; by K. Hantelmann, M. Kollecker, D. Hull, B. Hitzmann, T. Scheper.

* cited by examiner

DISPOSABLE BIOREACTOR COMPRISING A SENSOR ARRANGEMENT

The invention relates to a disposable bioreactor comprising a sensor arrangement, which can be reversibly fitted on the outside, for measuring a physical variable of a contained medium.

Such a bioreactor is known from US 2005/0163667 A1. Disclosed there is a disposable bioreactor that is designed as a bag and has in its interior a plurality of sensor cushions that are permanently connected to the transparent bag wall. The sensor cushions are fluorescence sensors, that is to say materials whose fluorescence properties change as a function of specific physical conditions, in particular dissolved oxygen, pH value or $CO_2$ content of the medium located in the bioreactor. The detector arrangement can be fitted outside the bag wall in the region of each sensor cushion. The detector arrangement respectively comprises a light source and a photodetector that is connected to an evaluation circuit. The light source radiates excitation light through the transparent bag wall onto the sensor cushion, whose fluorescent light is detected by the photodetector. The evaluation circuit is used to analyze specific properties of the detected fluorescent light, and to infer the photophysical conditions in the sensor cushion, that is to say the magnitude of the values to be determined. The known device constitutes a bioreactor comprising a sensor system that can already be sterilized at the manufacturers. Disposable bioreactors are usually sterilized with gamma radiation or very aggressive chemicals such as ethylene oxide (ETO). The problem frequently arises in this case that the sensor system, in particular the sensor electronics, does not withstand such a sterilization step. In the case of the known device, the sensor system is therefore split up into a portion that touches the medium in the interior of the bioreactor and is robust against sterilization, and a more sensitive part that can be fitted on the outside, in particular the sensor electronics, which can be fitted without sterility on the part of the user.

It is a disadvantage of the known device that it is based on sensor cushions that touch the medium. As previously explained, these sensor cushions must be resistant to the sterilization by gamma radiation or chemicals such as ETO. That is to say, such a treatment is not permitted to impair their fluorescence properties or, in particular, their dependence on the variables to be measured. This poses very narrow limits on the selection of the sensor cushions. On the other hand, there is a further limitation owing to the fact that for their part the sensor cushions are not permitted to influence the medium in the bioreactor. In particular, when use is made of the disposable bioreactor as a cell culture vessel there is the risk of an excessively intimate interaction between the cells and the sensor cushions.

It is the object of the present invention to develop a disposable reactor of the generic type in such a way that the interaction between sensor and medium is minimized.

This object is achieved in conjunction with a disposable bioreactor [the features of the preamble of claim 1] in such a way that there is integrated in at least one peripheral line of the bioreactor serving to supply and/or discharge medium a sensor adaptor for holding an electronic sensor arrangement interacting with medium flowing through the peripheral line via an internal boundary surface of the sensor adaptor.

The invention combines two basic features. Firstly, otherwise than in the case of the prior art the measuring location is situated not in the region of the reactor wall, but in the region of a peripheral line of the bioreactor. This has the advantage that there is an interaction between sensor and medium only during the comparatively short time when the medium is flowing through the peripheral line. Secondly, the present invention avoids a direct interaction between the sensor and the medium. Rather, it is provided that the data acquisition takes place through a boundary surface of the sensor adaptor, it being possible for the boundary surface to be configured so that there is only a minimum interaction between it and the medium. The inventive sensor adaptor is integrated in a region of the peripheral line that can be sterilized with the disposable reactor. It essentially comprises a continuation or an insert of the peripheral line comprising conduit boundary surfaces made from a suitable material, that is to say material that withstands gamma sterilization and/or ETO sterilization and is transparent to the physical variable to be measured, and/or to the corresponding sensor means. Furthermore, the sensor adaptor comprises connecting means for an electronic sensor arrangement tuned to the variable to be measured. In this case, the connecting means preferably comprise aligning means so that the sensor arrangement can easily be fastened on the sensor adaptor for example by being clipped into or pushed into it.

In a preferred embodiment of the invention, the sensor adaptor is integrated in an exhaust gas line. The invention is not limited in principle to a supply or discharge line, nor to a liquid or gaseous medium. However, it is particularly advantageous to integrate the sensor adaptor in a peripheral line that serves to remove gaseous medium. Particularly in the case of the use of the disposable bioreactor as a cell culture vessel, the chemical composition of the exhaust gas constitutes a very good indicator of the conditions in the cell culture. In particular, the $CO_2$ content of the exhaust gas permits inferences relating to the state of health of the cell culture.

In a preferred embodiment of the invention, the sensor arrangement is set up to interact directly with the medium through the internal boundary surface. In particular, it can be provided that the sensor arrangement comprises an infrared transmitter for emitting an infrared light through the boundary surface into the medium, and an infrared detector for detecting portions of the light emitted by the infrared transmitter after interaction with the medium. Thus, for example, it is possible to determine $CO_2$ content, already mentioned above, of the exhaust gas with the aid of infrared absorption and/or infrared scattering. What is involved here is a direct interaction of the sensor arrangement with the medium through the boundary surface. In this case, the boundary surface is preferably a glass, crystal or plastic surface transparent in the infrared spectral region. Particularly in the case of selection of a plastic surface, it is necessary to ensure the required resistance, already mentioned, against the provided sterilization.

As an alternative to direct measurement through the boundary surface, it can be provided in the case of a likewise advantageous embodiment of the invention that the measurement is performed by indirect interaction between the sensor arrangement and the medium, with the boundary surface also taking part. An example of this is an embodiment in which the sensor arrangement comprises a temperature detector that detects the temperature of the boundary surface. In this case, the temperature of the boundary surface would be varied by interaction with the medium, and would be detected by the sensor arrangement. It is advantageous in this case when the boundary surface consists of a medium-tight, thermally conducting material, it being also necessary here to ensure the resistance to sterilization.

As a further example of an indirect measurement in which the boundary surface also takes part, it can be provided in an alternative embodiment that the sensor arrangement comprises a voltage source and two electrodes connected thereto, and a measuring arrangement for detecting a current and/or a voltage between the electrodes, and that the boundary surface comprises two electrically conducting, mutually insulated subsurfaces, each of the electrodes being in electrically conducting contact with in each case one of the subsurfaces. This includes the case in which the boundary surfaces themselves form the electrodes. With such an embodiment, it is possible, for example, to measure the conductivity of the medium flowing through the peripheral line. Here, as well, the boundary surface itself is incorporated into the measurement. Of course, it is also necessary here to ensure the resistance of the boundary surface material to sterilization.

It holds for all the above-mentioned embodiments that an interaction, going beyond the measurement, between the boundary surface and the medium, for example a chemical reaction or a discharge of particles into the medium, be suppressed as far as possible.

Figure 2:
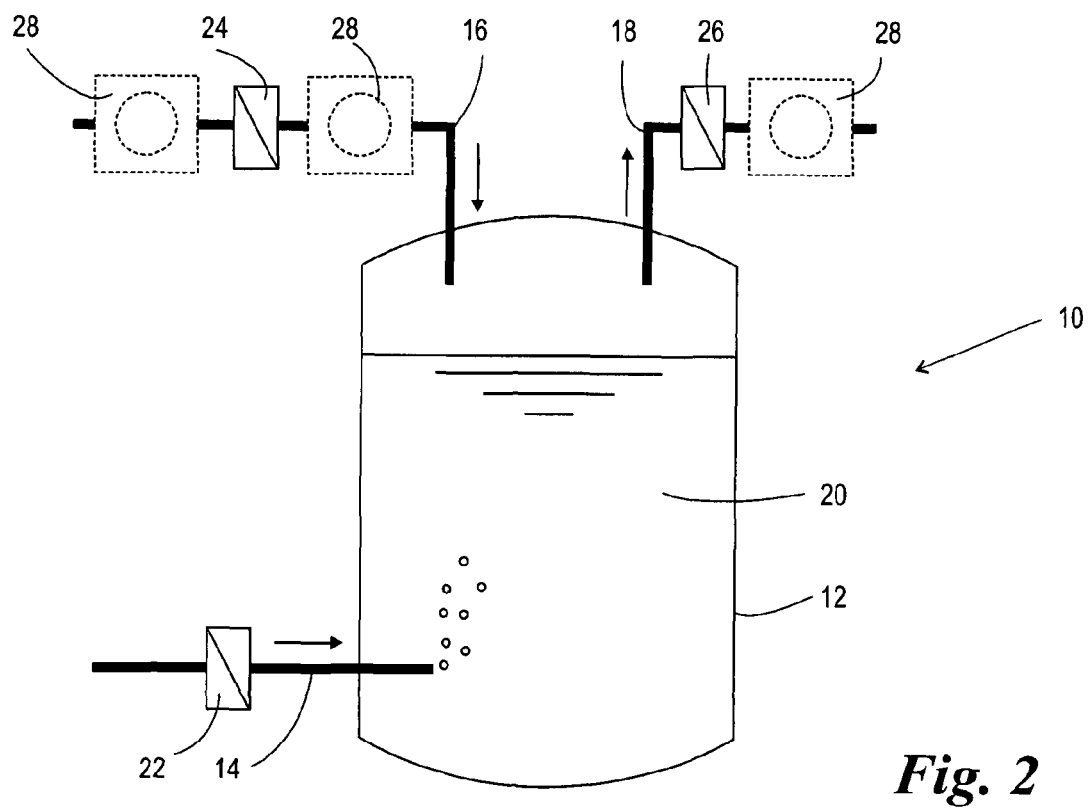
Figure 3:
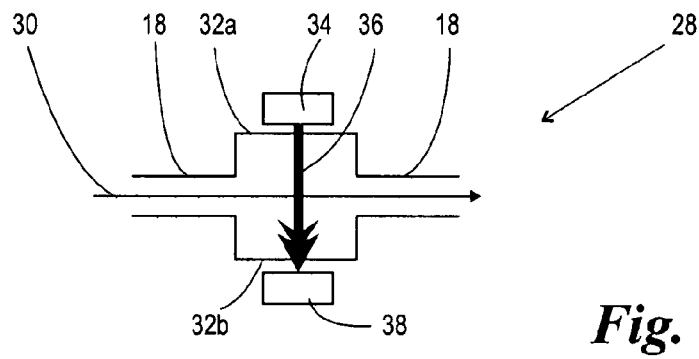
Figure 4:
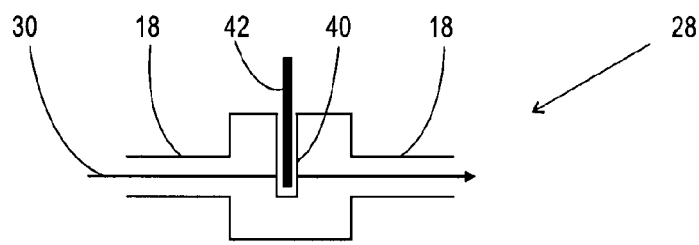
Figure 5:
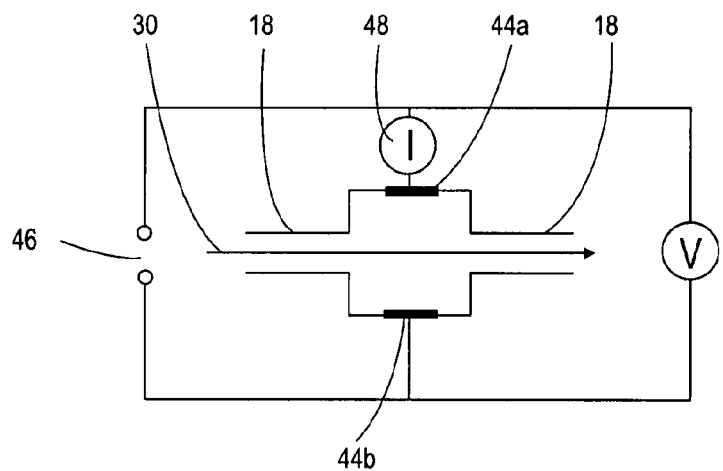
Figure 6:
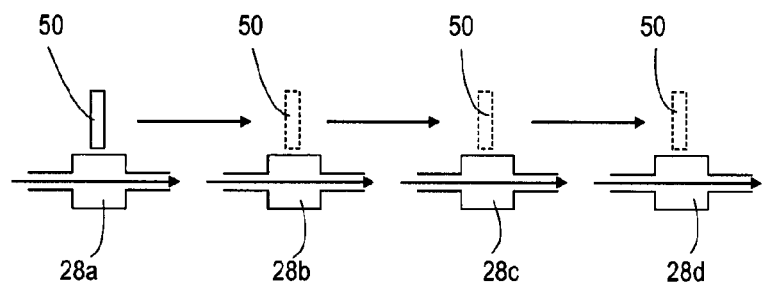

Further features and advantages of the invention emerge from the following special description in conjunction with the drawings, in which, FIG. 1 shows a schematic of a preferred embodiment of an inventive disposable bioreactor comprising a sensor adaptor in the sterile region of a degassing line, FIG. 2 shows a schematic of the disposable bioreactor of FIG. 1 with an alternative proposed arrangement for the sensor adaptor, FIG. 3 shows a schematic detailed view of a sensor adaptor provided for optical measurements, FIG. 4 shows a schematic detailed view of a sensor adaptor provided for temperature measurements, FIG. 5 shows a schematic detailed view of a sensor adaptor provided for conductivity measurements, and FIG. 6 shows a schematic of an automated periodic drive of a number of sensor adaptors by a common sensor device.

FIG. 1 shows a schematic of an inventive disposable bioreactor 10. The disposable bioreactor 10 is preferably configured as a foldable bag having a bag wall 12 and, permanently connected thereto, peripheral lines 14, 16 and 18. The peripheral line 14 is a gassing line via which gas is introduced into a liquid medium 20 contained in the bag 12. The peripheral line 16 is an inflow line for liquid and/or gaseous medium, and the peripheral line 18 is a degassing line. Further peripheral lines (not illustrated in FIG. 1) can likewise be provided for supplying or removing liquid or gaseous medium.

All the peripheral lines 14, 16 and 18 are each provided with a sterile filter 22, 24 and 26, respectively, in the embodiment illustrated in FIG. 1. The sterile filters 22, 24 and 26 ensure that the sterile disposable bioreactor 10 delivered to the user is not inadvertently contaminated.

In the case of the embodiment illustrated in FIG. 1, a sensor adaptor 28 is integrated in the peripheral line 18 upstream of the sterile filter 26. The sensor adaptor 28 constitutes an insert in the peripheral line 18, that is to say the outflowing gas can flow through the sensor adaptor 28. The sensor adaptor 28 is fabricated from a material that is resistant to the required sterilization of the bioreactor 10, which can vary in a fashion specific to application. Particularly advantageous sterilization methods are gamma sterilization and chemical sterilization with ETO. Furthermore, the choice of material of the sensor adaptor is tuned to the special sensor system to be adapted. Examples of this are explained further below.

FIG. 2 shows a schematic of the bioreactor of FIG. 1 with further options for fitting the sensor adaptor 28. The sensor adaptors 28 are illustrated by dashes in FIG. 2 in order to illustrate the optional nature of the arrangements. The arrangement of the sensor adaptor that is implemented in the individual case is to be selected by the person skilled in the art with reference to the variable to be measured and with regard to the accessibility thereof. Embodiments with a number of sensor adaptors, which can be of the same or different design, are conceivable.

FIG. 3 shows a particular embodiment of a sensor adaptor 28 for optical measurements. As indicated by the arrow 30, the sensor adaptor 28 is flowed through by a medium, in particular the exhaust gas, that flows through the peripheral line 18. The sensor adaptor has a pair of oppositely situated windows 32a and 32b that are transparent to infrared radiation. An infrared transmitter 34 transmits an infrared beam 36 through the input window 32a, the medium 30 flowing through the sensor adaptor, and the output window 32b. The infrared beam 36 is received by an infrared detector 38 that is connected to an evaluation unit (not illustrated in FIG. 3). By evaluating optical properties of the received beam 36, it is then possible to infer properties of the medium 30 flowing through. The $CO_2$ content in the exhaust gas of a cell culture cultivated in the disposable bioreactor can be measured with particular advantage by this method of IR analysis of the gas. The physical details of such a measurement are known from breathing air analysis as a field of medicine.

FIG. 4 shows an alternative embodiment of a sensor adaptor 28. The sensor adaptor has a depression that is surrounded by a thermally conducting wall section and reaches into the interior of the through-flow volume such that the gas 30 flowing through the sensor adaptor 28 flows around the wall section 40. This brings about a heat exchange between the gas and the wall area 40. The temperature of the wall area 40 can be detected by means of a temperature sensor 42, and it is possible to infer the temperature of the gas.

FIG. 5 shows a further embodiment of a sensor adaptor, which can be used here to measure the conductivity of the medium 30 flowing through. The sensor adaptor 28 has wall areas 44a and 44b that are electrically conducting and electrically insulated from one another and that are connected to a power supply unit 46 and a current measuring arrangement 48. When an electrically conducting medium is flowing through between the wall areas 44a and 44b acting as electrodes, an electric current can flow whose measurement permits conclusions to be reached concerning the electrical conductivity of the medium 30.

FIG. 6 shows a particularly advantageous application of the inventive disposable bioreactor comprising a sensor adaptor. The sensor adaptors 28a, 28b, 28c and 28d of various disposable bioreactors are illustrated in FIG. 6 as their representatives. An individual sensor, which can, for example, be an ocular sensor corresponding to FIG. 3, a thermal sensor corresponding to FIG. 4, a conductivity sensor corresponding to FIG. 5, or another sensor tuned to the sensor adaptors 28a, 28b, 28c and 28d, is preferably applied successively in an automated fashion to each of the sensor adaptors 28a, 28b, 28c and 28d, in order to carry out a measurement, and is subsequently moved on to the next sensor adaptor. This is possible without risk of contaminating the disposable bioreactor, since the sensor 50 runs into contact only with the exterior or with the prescribed coupling points of the sensor adaptors. In order to facilitate this, it is possible to provide the sensor adaptors in the figures with aligning and coupling means (not illustrated) such as, for example, latching devices, centering aids and/or rail systems.

Of course, the embodiments discussed in the special description and illustrated in the figures constitute only illustrative exemplary embodiments of the present invention. The person skilled in the art has a wide spectrum of modification options to hand. In particular, the selection of materials and forms is to be tuned to the special application, the envisaged sterilization methods and the measurement principles to be used.

The invention claimed is:

1. A disposable bioreactor comprising: a disposable container (12), at least one peripheral inflow line (14, 16) for delivering a gas or liquid into the container (12) and at least one peripheral outflow line (18) for removing gas from the container (12), at least one sensor arrangement reversibly fitted outside the container (12) in at least the peripheral outflow line (18) that removes gas from the container for measuring a physical variable of a medium flowing through the respective peripheral line (14, 16, 18) of the bioreactor, the sensor arrangement comprising a sensor adaptor (28) defining an insert in the respective peripheral line (14, 16, 18) and having an inlet end communicating with an upstream part of the respective peripheral line, an outlet end communicating with a downstream part of the respective peripheral line and a through passage extending between the inlet and outlet ends configured for accommodating a flow of the medium therethrough, the sensor adaptor being formed from a material that is resistant to sterilization applied to the disposable container, the sensor adaptor (28) further being configured for releasably holding an electronic sensor arrangement (34, 38; 42; 44a, 44b, 46, 48) that measures characteristics of the medium flowing through the peripheral line (14, 16, 18) via an internal boundary surface (32a, 32b; 40; 44b) of the sensor adaptor (28) while avoiding direct interaction between the electronic sensor arrangement (34, 38; 42; 44a, 44b,46,48) and the medium, the electronic sensor arrangement (34, 38; 42; 44a, 44b, 46, 48) comprising at least one of an infrared sensor (34, 38), a temperature sensor (42) and an electrical current or electrical voltage sensor (44a, 44b).

2. The disposable bioreactor as claimed in claim wherein the at least one sensor arrangement further comprises a sensor arrangement having a sensor adaptor (28) integrated in an inflow line (16) for liquid or gaseous medium.

3. The disposable bioreactor as claimed in claim 2, wherein the exhaust gas line (18) further includes a filter (26), the sensor adaptor (28) being between the container (12) and the filter (26), whereby the filter prevents contamination of the disposable container and the sensor adaptor after sterilization.

4. The disposable bioreactor as claimed in claim 1, characterized in that the sensor arrangement (34, 38; 41; 44a, 44b, 46, 48) is set up to interact directly with the medium through the internal boundary surface (32a, 32b; 40; 44a, 44b).

5. The disposable bioreactor as claimed in claim4, characterized in that the sensor arrangement comprises an infrared transmitter (34) for emitting an infrared light through the boundary surface (32a, 32b) into the medium, and an infrared detector (38) for detecting portions of the light emitted by the infrared transmitter (34) after interaction with the medium.

6. The disposable bioreactor as claimed in claim 5, characterized in that the boundary surface (32a, 32b) is a glass, crystal or plastic surface transparent in the infrared spectral region.

7. The disposable bioreactor as claimed in claim 1, characterized in that the sensor arrangement comprises a temperature detector (42) that detects the temperature of the boundary surface (40).

8. The disposable bioreactor as claimed in claim 7, characterized in that the boundary surface (40) consists of a thermally conducting material that avoids direct interaction between the sensor arrangement and the medium.

9. The disposable bioreactor as claimed in claim 1, characterized in that the sensor arrangement comprises a voltage source (46) and two electrodes (44a, 44b) connected thereto, and a measuring arrangement (48) for detecting a current and/or a voltage between the electrodes (44a, 44b), and in that the boundary surface comprises two electrically conducting, mutually insulated subsurfaces, each of the electrodes (44a, 44b) being in electrically conducting contact with in each case one of the subsurfaces.

10. The disposable bioreactor as claimed in claim 1, characterized in that the sensor adaptor (28) consists of a material resistant to gamma radiation.

11. The disposable bioreactor as claimed in claim 1, characterized in that the sensor adaptor (28) consists of a material resistant to ETO.

12. The disposable bioreactor as claimed in claim 1, wherein the at least one sensor arrangement comprises at least one sensor arrangement in the peripheral inflow line (16) and at least one sensor arrangement in the peripheral outflow line (18).

* * * * *